United States Patent [19]

Lin et al.

[11] Patent Number: 4,554,375

[45] Date of Patent: Nov. 19, 1985

[54] CO-PREPARATION OF 2,7-OCTADIENYL FORMATE, 1,6-OCTADIENE AND 4 VINYLCYCLOHEXENE FROM BUTADIENE USING A PLATINUM CATALYST

[75] Inventors: Jiang-Jen Lin, Round Rock; David C. Alexander, Austin both of Tex.

[73] Assignee: Texaco Inc., White Plains, N.Y.

[21] Appl. No.: 589,804

[22] Filed: Mar. 15, 1984

[51] Int. Cl.$^4$ ............................................. C07C 67/04
[52] U.S. Cl. .................................... 560/244; 585/366; 585/601
[58] Field of Search ......................................... 560/244

[56] References Cited

U.S. PATENT DOCUMENTS 3,795,699 3/1974 Wright ................................. 560/244
3,872,153 3/1975 Wright ................................. 560/244
3,923,875 12/1975 Rose ..................................... 560/244

FOREIGN PATENT DOCUMENTS 4408 10/1979 European Pat. Off. .
1326454 8/1973 United Kingdom ................. 560/244

*Primary Examiner*—Michael L. Shippen
*Attorney, Agent, or Firm*—Jack H. Park; Kenneth R. Priem

[57] ABSTRACT

A method for preparing 2,7-octadienyl formate by reacting 1,3-butadiene with formic acid in the presence of a platinum(II) catalyst is described. The platinum(II) catalyst is preferably platinum acetylacetonate. A reaction temperature between 50° and 150° C. is preferred, and carbon dioxide and a solvent may also be employed. Tetrahydrofuran and acetone are the preferred aprotic solvents.

2 Claims, No Drawings

CO-PREPARATION OF 2,7-OCTADIENYL FORMATE 1,6-OCTADIENE AND 4 VINYLCYCLOHEXENE FROM BUTADIENE USING A PLATINUM CATALYST

CROSS-REFERENCE TO RELATED APPLICATION

This application is related to U.S. patent application Ser. No. 589,805, filed on Mar. 13, 1984 which concerns the reductive dimerization of 1,3-butadiene with formic acid in the presence of a platinum catalyst and a polymeric amine promoter.

BACKGROUND OF THE INVENTION

1. Field of the Invention

The invention relates to the preparation of 2,7-octadienyl formate by the reaction of 1,3-butadiene with formic acid and more particularly relates to such a process conducted in the presence of a platinum catalyst.

2. Other Processes in the Field of the Invention

Linear dimerization of butadiene (1,3-butadiene) provides a source of $C_8$ unsaturated hydrocarbon intermediates useful for the synthesis of diacids, diesters, diols, or diamines. Linear oligomerization of butadiene typically results in the formation of n-octatriene products, and in particular either 1,3,6-octatriene or 1,3,7-octatriene. Unfortunately, such compounds are unreactive in many reactions or give complex reaction mixtures. 1,7-Octadiene and 1,6-octadiene are typical products. 1,6-Octadiene may be used in the production of decanediol or 1,7-octadiene.

The dimerization of olefins is a well known reaction. U.S. Pat. No. 3,562,351 describes a method for dimerizing and co-dimerizing monoolefins in the presence of a Group VIII water-soluble metal salt which is activated by treatment with an organometallic compound. The Group VIII metal is preferably nickel, cobalt or mixtures thereof. A rhodium catalyst is useful in synthesizing dienes from alphamonoolefins and conjugated dienes according to U.S. Pat. No. 3,565,821. Further, U.S. Pat. No. 3,848,015 teaches the production of dimers and trimers using a carbonyl moiety-free complex of a transition metal of Group VIII and an electron donor. The Group VIII transition metal is listed as being iron, cobalt, nickel, ruthenium, rhodium, palladium, osmium, iridium and platinum, although the preferred metals therein are iron, cobalt and nickel, nickel being especially preferred. Dimerization of diolefins may also be effected by maintaining the olefins in inert solvent solution in contact with a catalyst which is the product of the interaction between two metal complexes, each of which is a nitrosyl and/or carbonyl ligand, as seen in U.S. Pat. No. 3,917,730.

A general review of butadiene telomerization is given by R. Baker in "$\pi$-Allylmetal Derivatives in Organic Synthesis", Chemical Reviews, Vol. 73 (1973), No. 5, pp. 491–493. Transition metal catalysts mentioned therein include triallyl cobalt, $Co_2(CO)_8$, cobalt (II) chloride, cobalt acetylacetonate, ferric acetylacetonate, ferric chloride, nickel chloride, $\pi$-allylpalladium chloride and $(Ph_3P)_2Pd$ (maleic anhydride)$_2$. Tetrakis(triphenylphosphine)platinum is also mentioned as yielding mainly vinyl cyclohexene from the dimerization of butadiene in benzene solution.

Palladium catalysts are particularly popular for the co-dimerization of 1,3-butadiene and ethylene. U.S. Pat. No. 3,920,763 employs a $\pi$-allyl complex catalyst for this purpose which comprises a palladium source, a monotertiary phosphine electron donor ligand, a combination reducing agent and Lewis acid and an acidic, solid, silica-based support material. A dienophile-coordinated palladium-phosphine complex such as bis-(triphenylphosphine)-(maleic anhydride) palladium is the preferred catalyst for co-dimerization and homo-dimerization of butadienes in U.S. Pat. No. 3,925,497.

European Patent Application No. 0004408 teaches the preparation of 1,7-octadiene by the hydrodimerization of butadiene using a palladium-organophosphine catalyst which has been pre-treated with a reducing agent. The reducing agent may be formic acid, the triethylamine salt of formic acid, hydrazine, hydrogen or carbon monoxide. Palladium acetylacetonate is mentioned as a suitable palladium catalyst. Amine solvents may be used and carbon dioxide is taught as being able to increase the butadiene conversion. Two recent patents to Pittman, U.S. Pat. Nos. 4,243,829 and 4,377,719, and *J. Mol. Cat.*, Vol. 15 (1982), pp. 377–381 reveal processes for preparing 1,7-octadiene selectively by dimerizing butadiene in the presence of a catalytic amount of palladium and a teritiary phosphine including a solvent, a strong base and formic acid.

Certain platinum catalysts have also been shown to be useful in butadiene dimerizations. L. H. Slaugh, et al. in "A Novel Effect of Carbon Dioxide on Catalyst Properties. Dimerization of Butadiene", *Journal of the American Chemical Society*, Vol. 91, No. 21 (1969), pp. 5904–5, disclose that the presence of carbon dioxide enhances the yield to 1,3,7-octatriene over platinum, palladium and nickel catalysts. The metals are complexed with triphenyl phosphines and occasionally carbonyls. Platinum catalysts such as lithium tetrachloroplatinate(II) and $Pt(C_5H_7O_2)_2$ are used to make 1,7-octadiene from butadiene in the presence of dimethylformamide and formic acid as described in S. Gardner, et al., "Platinum-Metal Catalyzed Formation of Linear Octadienes", *Tetrahedron Letters*, No. 2 (1972), pp. 163–164. However, the selectivity to 1,6-octadiene is unsatisfactory. Octa-1,3,7-triene and octa-2,7-dienyl formate were ruled out as intermediates. Formate ester was produced only in trace amounts.

U.S. Pat. No. 3,732,328 teaches the production of an octadiene selected from the group consisting of octa-1,6-diene, octa-1,7-diene, monomethylocta-1,6-diene, monomethylocta-1,7-diene, dimethylocta-1,6-diene and dimethylocta-1,7-diene. Butadiene and/or isoprene at a temperature of 20° to 200° C. is contacted with a $10^{-1}$ to $10^{-5}$ molar concentration of a platinum, palladium or ruthenium catalyst, such as halides, alkanoates, acetylacetonates, bisbenzonitrile palladium(II) and lithium palladous chloride. Formic acid and a polar solvent must also be present. Dimethyl formamide is a preferred solvent. However, this process suffers from a low yield to 1,6-octadiene.

Similarly, U.S. Pat. No. 3,823,199 teaches that 1,6- and/or 1,7-octadienes may be produced by reacting 1,3-butadiene with metallic platinum, palladium, rhodium, ruthenium or osmium in the presence of formic acid. Preferably, a compound of one or more of these catalysts in a non-polar solvent such as benzene is employed. Selectivities of 1,6-octadiene are not disclosed, and no amine promoter is used.

S. Teranishi in *J. Org. Chem.*, Vol. 46 (1981), pp. 2356–2362, discloses a palladium(O) complex supported on a phosphinated polystyrene as a catalyst for the reaction of 1,3-butadiene and formic acid. In this case, 1,7-octadiene was produced exclusively. Octadienyl formates were specifically reported as not detected. European Patent Application 0043038 reports the production of carboxylic acids having nine carbons from the reaction of butadiene with formic acid.

Finally U.S. Pat. No. 4,334,117 reveals an improved process for the preparation of alkadienes by contacting butadiene or isoprene with a platinum or palladium catalyst, optionally in a sulfolane solution, in the presence of a tertiary lower alkylamine formate and at least one particularly-defined phosphine compound. Platinum acetylacetonate is specifically mentioned.

To our knowledge, the synthesis of octadienyl formates is considered to be a novel process.

SUMMARY OF THE INVENTION

The invention concerns a method for preparing 2,7-octadienyl formate by reacting 1,3-butadiene with formic acid in the presence of a platinum(II) acetylacetonate catalyst.

DETAILED DESCRIPTION OF THE PREFERRED EMBODIMENTS

The reaction of this invention may be stoichiometrically diagrammed as follows

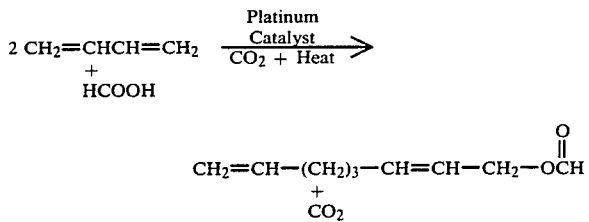

It may be seen that two moles of 1,3-butadiene should be used for every mole of formic acid. The molar ratio of butadiene to formic acid should range from 5:1 to 1:5, preferably. In practice, a slight excess of 1,3-butadiene is preferred.

The catalyst should be a platinum catalyst, preferably a platinum(II) catalyst. Various possible platinum(II) catalysts include $PtCl_2$, $PtBr_2$, $(PhCN)_2PtCl_2$, $(Ph_3P)_2PtCl_2$. Ligand stabilized Pt(O) compounds such as $(Ph_3P)_4Pt$ might also be found to be useful. In these formulas, Ph designates a phenyl group. The most preferred catalyst is platinum acetylacetonate abbreviated $Pt(acac)_2$. The molar ratio of butadiene reactant to platinum catalyst is preferably 10,000:1 to 1000:1.

The preferred reaction temperature is 50° to 150° C. with an especially preferred temperature of about 100° C. Although carbon dioxide is not essential to the reaction, its presence is preferred. A $CO_2$ partial pressure of about 50 to 500 psi is preferred.

A solvent may also be present to help facilitate the reaction. Any organic solvent such as alcohols and esters may be used, but aprotic, polar or non-polar solvents are preferred. Such preferred solvents include oxygenates such as tetrahydrofuran (THF) and other ethers and aromatics such as toluene, chlorobenzene, nitrobenzene, benzonitrile and the like. Acetone and THF are especially preferred.

2,7-Octadienyl formate is expected to be useful in the production of carboxylic acids containing nine carbon atoms via formate rearrangement similar to the mechanism for making acetic acid from methyl formate described in U.S. Pat. No. 4,194,056. Alcohols and aldehydes having eight carbon atoms could be made from 2,7-octadienyl formate via hydrolysis. 2,7-Octadienyl formate may also be an intermediate to other diols, amines and carboxylic acids by way of reaction of the terminal olefin.

The invention will be further illustrated by the following experimental examples. These examples are not intended to limit the invention beyond the spirit and scope thereof defined in the appended claims. It is expected that one skilled in the art could modify the invention in terms of changing catalyst/promoter types and proportions, temperatures and pressures outside these specific examples but still remain within the spirit and scope of the claims.

EXAMPLE 1

To a 300 ml stainless steel magnedrive reactor were charged platinum(II) acetylacetonate (0.039g, 0.1 mm), formic acid (12.0 g, 0.26 mmoles) and THF (6.0 g). The reactor was flushed with carbon dioxide, then charged with 1,3-butadiene (45 g) and carbon dioxide to 100 psi total pressure. The system was heated to 118° C. within a 20 minute period. Then the reaction temperature was maintained within the range of 118°–124° C for the period of 1.5 hours. The maximum pressure was 420 psi during the reaction period. The system was cooled and then the excess gas was vented. A very light yellow solution (25.8 g) was recovered, which gave the following gas chromatography analysis:

| | |
|---|---:|
| 1,3-Butadiene, % | 23.8 |
| THF, % | 17.8 |
| 1,7-Octadiene, % | 3.0 |
| 1,6-Octadiene, % | 21.0 |
| 4-Vinylcyclohexene, % | 17.6 |
| 2,7-Octadienyl formate, % | 12.9 |

The production of 2,7-octadienyl formate was calculated to be 22,000 g/g-atm-Pt/hr based on Pt catalyst charged. This value is called "turnover". Other examples conducted according to this procedure can be found in Table I.

TABLE I 2,7-OCTADIENYL FORMATE SYNTHESIS FROM BUTADIENE AND FORMIC ACID

| Example | Catalyst | Formic Acid, g | Solvent Used | Butadiene Charged, g | Initial & Max. $CO_2$ Pressure, psi | Reaction Temp. & Time, °C. | 2,7-Octadienyl Formate Weight, g | Turnover | 1,6-Octadiene, g | 1,7-Octadiene, g | 4-Vinyl-cyclohexene, g |
|---|---|---|---|---|---|---|---|---|---|---|---|
| 1 | Pt(acac)$_2$ (0.039 g, 0.1 mm) | 12.0 | THF (6.0 g) | 45 | 100–420 | 118–124 1.5 hr | 3.4 | 22,000 g/g-atm-Pt/hr | 5.4 | 0.8 | 4.6 |
| 2 | Pt(acac)$_2$ (0.039 g, 0.1 mm) | 18.0 | THF (6.0 g) | 60 | 100–520 | 103–133 4.5 hr | 1.7 | 11,000 g/g-atm-Pt/hr | 21.5 | — | 3.6 |

TABLE I-continued
2,7-OCTADIENYL FORMATE SYNTHESIS FROM BUTADIENE AND FORMIC ACID

| Example | Catalyst | Formic Acid, g | Solvent Used | Butadiene Charged, g | Initial & Max. CO$_2$ Pressure, psi | Reaction Temp. & Time, °C. | 2,7-Octadienyl Formate Weight, g | Turnover | 1,6-Octadiene, g | 1,7-Octadiene, g | 4-Vinylcyclohexene, g |
|---|---|---|---|---|---|---|---|---|---|---|---|
| 3 | Pt(acac)$_2$ (0.039 g, 0.1 mm) | 12.0 | THF (6.0 g) | 45 | 100–680 | 115 5.5 hr | 0.86 | 1,600 g/g-atm-Pt/hr | 2.6 | 0.26 | 4.8 |
| 4 | Pt(acac)$_2$ (0.039 g, 0.1 mm) | 6.0 | Acetone (6.0 g) | 65 | 150–510 | 119–122 3.0 hr | 1.6 | 5,300 g/g-atm-Pt/hr | 3.3 | 0.35 | 6.5 |
| 5 | Pt(acac)$_2$ (0.039 g, 0.1 mm) | 18.0 | None | 32 | 110–430 | 100–125 ~5.0 hr | 0.32 | 640 g/g-atm-Pt/hr | 0.36 | 0 | 1.32 |
| 6 | Pd(PPh$_3$)$_4$ (0.115 g, 0.1 mm) | 6.0 | Acetone (6.0 g) | 65 | 170–650 | 110–120 3.0 hr | 0 | 0 | 2.1 | 2.8 | 5.2 |

It may be noted that 1,6-octadiene and 4-vinylcyclohexene are also produced in appreciable yields. 1,6-Octadiene is well known as a valuable chemical and may be separated out of the product stream. The production of 1,6-octadiene is predominant over 1,7-octadiene. The relative ratio is greater than 85:15 (1,6-vs. 1,7-octadiene) when platinum catalysts are used. 4-Vinylcyclohexene is produced through a thermal Diels-Alder reaction which can be minimized by using a larger volume continuous reactor without a preheating period as in the batch procedure used in the examples. In addition, 4-vinylcyclohexene is recognized as a useful chemical for styrene synthesis.

The comparative Example 6 showed there is no 2,7-octadienyl formate produced by using a palladium catalyst.

We claim:

1. A method for the preparation of 2,7-octadienyl formate, 1,6-octadiene and 4-vinylcyclohexene comprising reacting 1,3-butadiene with formic acid at a mole ratio of butadiene to formic acid of from 5:1 to 1:5 in the presence of a platinum (II) acetyl acetonate catalyst optionally in the presence of a solvent from the group consisting of oxygenated solvents and aromatic solvents at a temperature in the range between 50° to 150° C. and at a CO$_2$ partial pressure between about 50 and 500 psi where the mole ratio of butadiene to platinum catalyst ranges from 10,000:1 to 1,000:1.

2. The method of claim 1 in which the solvent is selected from the group consisting of tetrahydrofuran and acetone.

* * * * *